(12) United States Patent
Carter

(10) Patent No.: US 9,636,142 B2
(45) Date of Patent: May 2, 2017

(54) BUTTON PORT

(71) Applicant: Covidien LP, Mansfield, MA (US)

(72) Inventor: Sally Carter, Nashua, NH (US)

(73) Assignee: Covidien LP, Mansfield, MA (US)

( * ) Notice: Subject to any disclaimer, the term of this patent is extended or adjusted under 35 U.S.C. 154(b) by 90 days.

(21) Appl. No.: 14/309,978

(22) Filed: Jun. 20, 2014

(65) Prior Publication Data
US 2014/0303444 A1  Oct. 9, 2014

Related U.S. Application Data

(62) Division of application No. 12/467,451, filed on May 18, 2009, now Pat. No. 8,795,161.

(60) Provisional application No. 61/075,548, filed on Jun. 25, 2008.

(51) Int. Cl.
*A61B 17/34* (2006.01)
*A61B 17/02* (2006.01)

(52) U.S. Cl.
CPC ...... *A61B 17/3423* (2013.01); *A61B 17/0218* (2013.01); *A61B 17/3431* (2013.01); *A61B 2017/0225* (2013.01); *A61B 2017/3433* (2013.01); *A61B 2017/3484* (2013.01)

(58) Field of Classification Search
CPC ........ A61B 17/0218; A61B 2017/0225; A61B 17/3423; A61B 17/3431; A61B 2017/3484
USPC .......................... 600/201, 208, 184; 606/108
See application file for complete search history.

(56) References Cited

U.S. PATENT DOCUMENTS

| 3,495,586 A | | 2/1970 | Regenbogen |
| 4,328,605 A | * | 5/1982 | Hutchison et al. ......... 24/115 G |
| 4,946,440 A | * | 8/1990 | Hall ...................... A61B 18/08 600/569 |
| 5,073,169 A | | 12/1991 | Raiken |
| 5,082,005 A | | 1/1992 | Kaldany |
| 5,273,529 A | * | 12/1993 | Idowu ................. A61J 15/0065 604/108 |
| 5,281,199 A | * | 1/1994 | Ensminger ........ A61M 39/0208 604/288.03 |
| 5,358,488 A | * | 10/1994 | Suriyapa ............. A61J 15/0015 604/103.03 |
| 5,360,417 A | | 11/1994 | Gravener et al. |
| 5,366,478 A | | 11/1994 | Brinkerhoff et al. |

(Continued)

FOREIGN PATENT DOCUMENTS

| EP | 1774918 A1 | 4/2007 |
| WO | 97/33520 | 9/1997 |

OTHER PUBLICATIONS

European Search Report for corresponding EP09251613 date of mailing is Mar. 24, 2011 (3 pages).

(Continued)

*Primary Examiner* — Kathleen Holwerda

(57) ABSTRACT

The present disclosure relates to a surgical apparatus for positioning within an incision in tissue. In one aspect of the present disclosure, the surgical access apparatus includes an elongated seal member configured to removably receive at least one surgical object, and a deployment member. In another of the present disclosure, the surgical access apparatus includes a housing configured to removably receive at least one surgical object, an elongated member, and at least one filament. A method of percutaneously accessing an underlying surgical work site using the surgical apparatus is also disclosed.

20 Claims, 9 Drawing Sheets

(56) References Cited

U.S. PATENT DOCUMENTS

| | | | |
|---|---|---|---|
| 5,431,676 A | 7/1995 | Dubrul et al. | |
| 5,437,683 A | 8/1995 | Neumann et al. | |
| 5,460,170 A * | 10/1995 | Hammerslag | 600/201 |
| 5,480,410 A | 1/1996 | Cuschieri et al. | |
| 5,514,133 A | 5/1996 | Golub et al. | |
| 5,524,644 A | 6/1996 | Crook | |
| 5,545,179 A | 8/1996 | Williamson, IV | |
| 5,634,937 A | 6/1997 | Mollenauer et al. | |
| 5,649,550 A | 7/1997 | Crook | |
| 5,653,705 A | 8/1997 | de la Torre et al. | |
| 5,683,378 A | 11/1997 | Christy | |
| 5,741,298 A | 4/1998 | MacLeod | |
| 5,782,817 A | 7/1998 | Franzel et al. | |
| 5,795,290 A | 8/1998 | Bridges | |
| 5,813,409 A | 9/1998 | Leahy et al. | |
| 5,820,600 A | 10/1998 | Carlson et al. | |
| 5,836,913 A * | 11/1998 | Orth | A61B 17/3417 604/107 |
| 5,848,992 A | 12/1998 | Hart et al. | |
| 5,865,817 A | 2/1999 | Moenning et al. | |
| 5,904,703 A | 5/1999 | Gilson | |
| 5,951,588 A | 9/1999 | Moenning | |
| 5,976,174 A | 11/1999 | Ruiz | |
| 6,024,736 A | 2/2000 | de la Torre et al. | |
| 6,033,426 A | 3/2000 | Kaji | |
| 6,033,428 A | 3/2000 | Sardella | |
| 6,110,154 A | 8/2000 | Shimomura et al. | |
| 6,142,936 A | 11/2000 | Beane et al. | |
| 6,228,063 B1 | 5/2001 | Aboul-Hosn | |
| 6,254,534 B1 | 7/2001 | Butler et al. | |
| 6,276,661 B1 | 8/2001 | Laird | |
| 6,315,770 B1 | 11/2001 | de la Torre et al. | |
| 6,382,211 B1 | 5/2002 | Crook | |
| 6,440,063 B1 | 8/2002 | Beane et al. | |
| 6,450,983 B1 | 9/2002 | Rambo | |
| 6,468,292 B1 | 10/2002 | Mollenauer et al. | |
| 6,558,371 B2 | 5/2003 | Dorn | |
| 6,582,364 B2 | 6/2003 | Butler et al. | |
| 6,589,208 B2 * | 7/2003 | Ewers | A61M 25/10 604/102.01 |
| 6,613,952 B2 | 9/2003 | Rambo | |
| 6,623,426 B2 | 9/2003 | Bonadio et al. | |
| 6,632,197 B2 * | 10/2003 | Lyon | A61B 17/3421 604/106 |
| 6,702,787 B2 | 3/2004 | Racenet et al. | |
| 6,723,088 B2 | 4/2004 | Gaskill, III et al. | |
| 6,814,078 B2 | 11/2004 | Crook | |
| 6,840,946 B2 | 1/2005 | Fogarty et al. | |
| 6,846,287 B2 | 1/2005 | Bonadio et al. | |
| 6,863,674 B2 | 3/2005 | Kasahara et al. | |
| 6,916,310 B2 | 7/2005 | Sommerich | |
| 6,945,932 B1 | 9/2005 | Caldwell et al. | |
| 6,958,037 B2 | 10/2005 | Ewers et al. | |
| 6,972,026 B1 | 12/2005 | Caldwell et al. | |
| 7,008,377 B2 | 3/2006 | Beane et al. | |
| 7,052,454 B2 | 5/2006 | Taylor | |
| 7,081,089 B2 | 7/2006 | Bonadio et al. | |
| 7,083,595 B2 * | 8/2006 | Chu | A61J 15/0015 604/107 |
| 7,163,510 B2 | 1/2007 | Kahle et al. | |
| 7,195,590 B2 | 3/2007 | Butler et al. | |
| 7,214,185 B1 | 5/2007 | Rosney et al. | |
| 7,238,154 B2 * | 7/2007 | Ewers et al. | 600/208 |
| 7,625,361 B2 | 12/2009 | Suzuki et al. | |
| 8,795,161 B2 | 8/2014 | Carter | |
| 2003/0093104 A1 | 5/2003 | Bonner et al. | |
| 2004/0015185 A1 | 1/2004 | Ewers et al. | |
| 2004/0049100 A1 | 3/2004 | Butler et al. | |
| 2004/0059297 A1 | 3/2004 | Racenet et al. | |
| 2004/0073090 A1 | 4/2004 | Butler et al. | |
| 2004/0092795 A1 | 5/2004 | Bonadio et al. | |
| 2004/0092796 A1 | 5/2004 | Butler et al. | |
| 2004/0267096 A1 | 12/2004 | Caldwell et al. | |
| 2005/0020884 A1 | 1/2005 | Hart et al. | |
| 2005/0090716 A1 | 4/2005 | Bonadio et al. | |
| 2005/0090717 A1 | 4/2005 | Bonadio et al. | |
| 2005/0148823 A1 | 7/2005 | Vaugh et al. | |
| 2005/0192483 A1 | 9/2005 | Bonadio et al. | |
| 2005/0203346 A1 | 9/2005 | Bonadio et al. | |
| 2005/0240082 A1 | 10/2005 | Bonadio et al. | |
| 2005/0251092 A1 | 11/2005 | Howell et al. | |
| 2005/0267419 A1 | 12/2005 | Smith | |
| 2005/0288558 A1 | 12/2005 | Ewers et al. | |
| 2006/0030755 A1 | 2/2006 | Ewers et al. | |
| 2006/0084842 A1 | 4/2006 | Hart et al. | |
| 2006/0129165 A1 | 6/2006 | Edoga et al. | |
| 2006/0149305 A1 | 7/2006 | Cuevas et al. | |
| 2006/0149306 A1 | 7/2006 | Hart et al. | |
| 2006/0161049 A1 | 7/2006 | Beane et al. | |
| 2006/0161050 A1 | 7/2006 | Butler et al. | |
| 2006/0241651 A1 | 10/2006 | Wilk | |
| 2006/0247498 A1 | 11/2006 | Bonadio et al. | |
| 2006/0247499 A1 | 11/2006 | Butler et al. | |
| 2006/0247500 A1 | 11/2006 | Voegele et al. | |
| 2007/0016134 A1 | 1/2007 | Suzuki et al. | |
| 2007/0088202 A1 | 4/2007 | Albrecht et al. | |
| 2007/0088204 A1 | 4/2007 | Albrecht et al. | |
| 2007/0088241 A1 | 4/2007 | Brustad et al. | |
| 2007/0093695 A1 | 4/2007 | Bonadio et al. | |
| 2007/0118175 A1 | 5/2007 | Butler et al. | |
| 2007/0149859 A1 | 6/2007 | Albrecht et al. | |
| 2007/0151566 A1 | 7/2007 | Kahle et al. | |
| 2007/0156023 A1 | 7/2007 | Frasier et al. | |
| 2007/0185387 A1 | 8/2007 | Albrecht et al. | |
| 2007/0203398 A1 | 8/2007 | Bonadio et al. | |
| 2007/0225569 A1 | 9/2007 | Ewers et al. | |
| 2008/0086167 A1 | 4/2008 | Mastri et al. | |
| 2008/0097332 A1 | 4/2008 | Greenhalgh et al. | |
| 2009/0105635 A1 | 4/2009 | Bettuchi et al. | |

OTHER PUBLICATIONS

Extended European Search Report from European Patent Application No. 11250370.1 mailed Jun. 29, 2011.

European Search Report Application No. 09 251 613.7, dated May 5, 2015.

Canadian Office Action for Canadian Application No. 2,666,883, dated May 19, 2015, 3 pages.

* cited by examiner

BUTTON PORT

CROSS-REFERENCE TO RELATED APPLICATIONS

This application is a divisional of U.S. patent application Ser. No. 12/467,451, filed May 18, 2009, now U.S. Pat. No. 8,795,161, which claims the benefit of U.S. Provisional Application No. 61/075,548, filed Jun. 25, 2008, and the disclosures of each of the above-identified applications are hereby incorporated by reference in their respective entireties.

BACKGROUND

1. Technical Field

The present disclosure relates to a surgical access apparatus for positioning within an incision in tissue. More particularly, the present disclosure relates to a surgical access apparatus that is adapted to removably receive one or more surgical objects, and configured for insertion into, and anchoring within, the incision.

2. Background of the Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

In general, during a minimally invasive procedure, a surgical access apparatus or portal member is used to facilitate access to the surgical site with surgical instrumentation, e.g., endoscopes, obturators, staplers, and the like. A typical surgical access apparatus defines a passageway or lumen through which the surgical instrumentation is inserted and the procedure is carried out.

While many varieties of surgical access apparatus are known in the art, a continuing need exists for a surgical access apparatus that may be releasably and reliably secured within the patient's tissue throughout the duration of the minimally invasive procedure.

SUMMARY

The present disclosure relates to a surgical apparatus for positioning within an incision in tissue. In one aspect of the present disclosure, the surgical access apparatus includes an elongated seal member defining a longitudinal axis and a deployment member.

The elongated seal member is adapted to transition between first and second conditions. In the first condition, the elongated seal member defines a first transverse dimension sufficient to facilitate securement of the elongated seal member within the incision and a tissue engaging portion configured to engage the tissue in substantially sealed relation. In the second condition, the elongated seal member defines a second transverse dimension, which is less than the first transverse dimension, to facilitate insertion of the elongated seal member within the incision.

The elongated seal member is at least partially composed of an at least semi-resilient material such that the elongated seal member is biased towards the first condition thereof. The elongated seal member includes a longitudinal passageway for the reception and passage of a surgical object in substantially sealed relation.

The elongated seal member includes a proximal end, which may include a stiffening member, and a distal end, which may include a lip. The stiffening member is adapted to facilitate anchoring of the elongated seal member within the incision, and in one embodiment thereof, may be generally annular in shape. The lip extends outwardly relative to the longitudinal axis, when the elongated seal member is in the first condition, and is dimensioned to engage the tissue to resist removal of the elongated seal member therefrom.

In one embodiment, the elongated seal member defines an internal cavity that is configured to retain a fluid therein, and in another embodiment, the elongated seal member defines a variable cross-sectional dimension along the longitudinal axis.

The deployment member of the surgical access apparatus is at least partially positionable within the longitudinal passageway of the elongated seal member. The deployment member is secured to the elongated seal member along an internal surface thereof such that distal longitudinal movement of the deployment member along the longitudinal axis causes the elongated seal member to transition from the first condition to the second condition. When subjected to a predetermined force, the deployment member may be detached from the elongated seal member to permit the deployment member to be removed from the longitudinal passageway with the elongated seal member in the first condition, thereby leaving the elongated seal member within the incision to receive the surgical object. The deployment member may be releasably secured to the elongated seal member with an adhesive.

In one embodiment, the deployment member includes a sleeve having an opening to receive at least one digit of a user to thereby facilitate grasping and removal of the deployment member from the elongated seal member.

In another aspect of the present disclosure, the surgical access apparatus includes a housing configured to removably receive at least one surgical object, an elongated member extending distally from the housing, and at least one filament secured to the elongated member and extending proximally relative thereto.

The housing includes locking structure configured to engage the at least one filament and thereby maintain the second condition of the elongated member. The locking structure includes at least one channel formed in the housing that is configured to at least partially receive the at least one filament. In one embodiment, the locking structure may include a locking member that is repositionable between unlocked and locked positions. In this embodiment, the locking member defines a channel therethrough that is configured to at least partially receive the at least one filament. In the unlocked position, the channel of the locking member and the channel formed in the housing are substantially aligned, and in the locked position, the channel of the locking member and the channel formed in the housing are substantially misaligned. The locking member may be biased towards the locked position by a biasing member.

The elongated member includes a tubular braid defining an axial lumen that is configured to allow the at least one surgical object to pass therethrough. The braid is formed of a mesh of fibers which may be either substantially elastic, or substantially inelastic.

The elongated member is adapted to transition from a first condition, in which the elongated member is configured for at least partial insertion within the incision, and a second condition, in which the elongated member defines a tissue engaging portion configured to facilitate anchoring of the elongated member within the patient's tissue.

The filament, or filaments, are dimensioned for grasping by a user such that drawing the at least one filament proximally transitions the elongated member from the first condition to the second condition. The filament, or filaments, may be disposed within the lumen of the elongated member, or externally thereof. The filament, or filaments, may alternatively be secured to an intermediate or distal portion of the elongated member.

In one embodiment, the surgical access apparatus further includes a membrane disposed about at least a proximal portion of the elongated member to facilitate anchoring of the elongated member within the tissue. The membrane may also facilitate passage of the at least one surgical object through the elongated member.

In another aspect of the present disclosure, a method of percutaneously accessing an underlying surgical work site is disclosed. The first step of the method includes providing a surgical access apparatus having an elongated seal member and a deployment member.

The elongated seal member defines a longitudinal axis, a proximal end, and a distal end. The elongated seal member has a longitudinal passageway for reception and passage of a surgical object and is adapted to transition between a first condition and a second condition. In the first condition, the elongated seal member defines a first transverse dimension, and in the second condition, the elongated seal member defines a second transverse dimension. The elongated seal member comprises an at least a semi-resilient material to be normally biased towards the first condition thereof.

The deployment member is at least partially positionable within the longitudinal passageway of the elongated seal member and is secured to the elongated seal member along an internal surface adjacent the distal end thereof. Upon distal longitudinal movement of the deployment member along the longitudinal axis, the elongated seal member is caused to transition from the first condition to the second condition.

The deployment member is advanced distally within the longitudinal passageway of the elongated seal member to thereby transition the elongated seal member into the second condition, and secure the elongated seal member within the incision. Subsequently, the surgical access apparatus is inserted into the incision, the deployment member is removed from the elongated seal member, and the surgical object is inserted into the longitudinal passageway and used to perform at least one surgical function. Thereafter, the surgical object is removed from the longitudinal passageway, the elongated seal member is removed from the incision, and the incision is closed.

BRIEF DESCRIPTION OF THE DRAWINGS

Various embodiments of the present disclosure are described hereinbelow with references to the drawings, wherein.

DETAILED DESCRIPTION OF THE EMBODIMENTS

Figure 1:
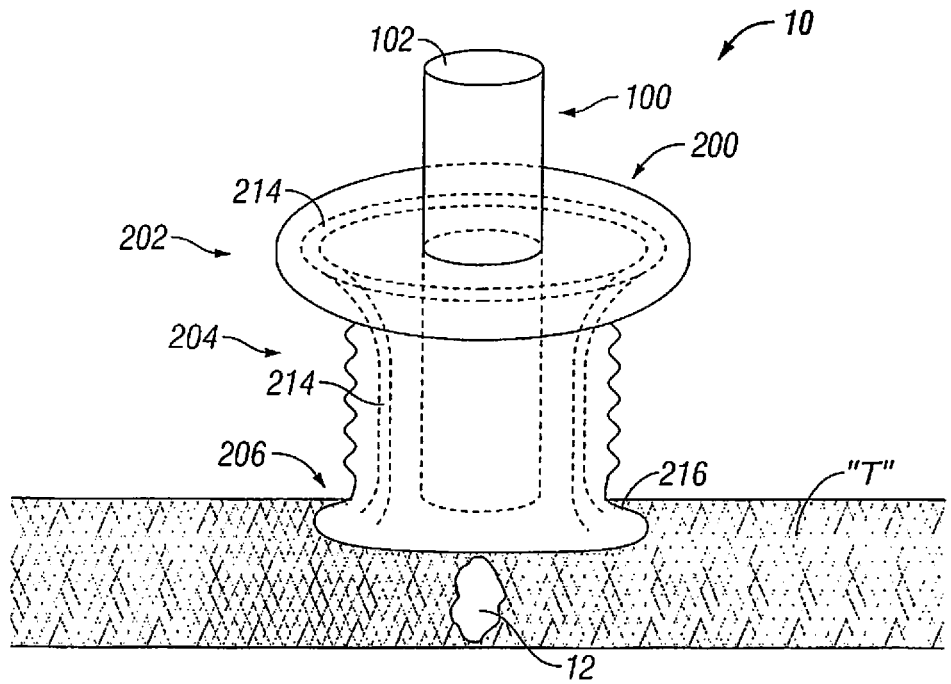
FIG. 1 is a perspective view of a surgical access apparatus including a seal member and a sleeve member in accordance with one aspect of the present disclosure.

In the drawings and in the description which follows, in which like references numerals identify similar or identical elements, the term "proximal" will refer to the end of the apparatus which is closest to the user during use, while the term "distal" will refer to the end which is furthest from the user. Additionally, the term "incision" should be understood as referring to any opening in a patient's tissue, whether formed by the user or pre-existing.

Figure 2A:
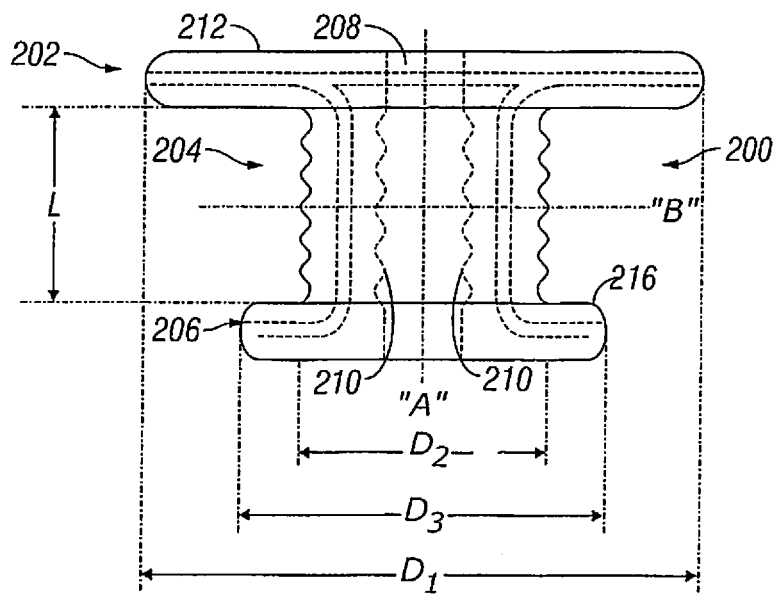
FIG. 2A is a side cross-sectional view of the seal member of FIG. 1 shown in a first condition with the sleeve member removed therefrom.
Figure 2B:
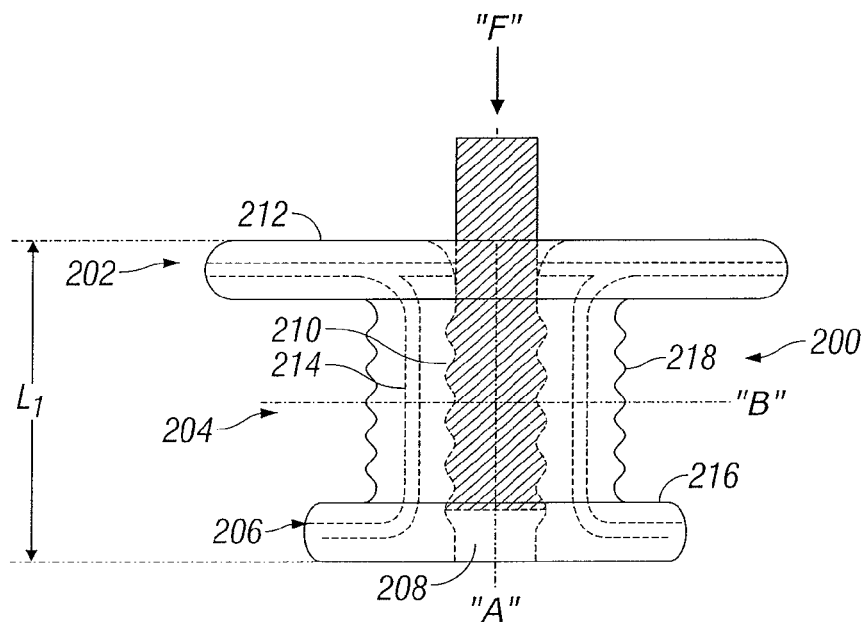
FIG. 2B is a side cross-sectional view of the seal member of FIG. 1 shown in a first condition with the sleeve member inserted therein and secured thereto.
Figure 3:
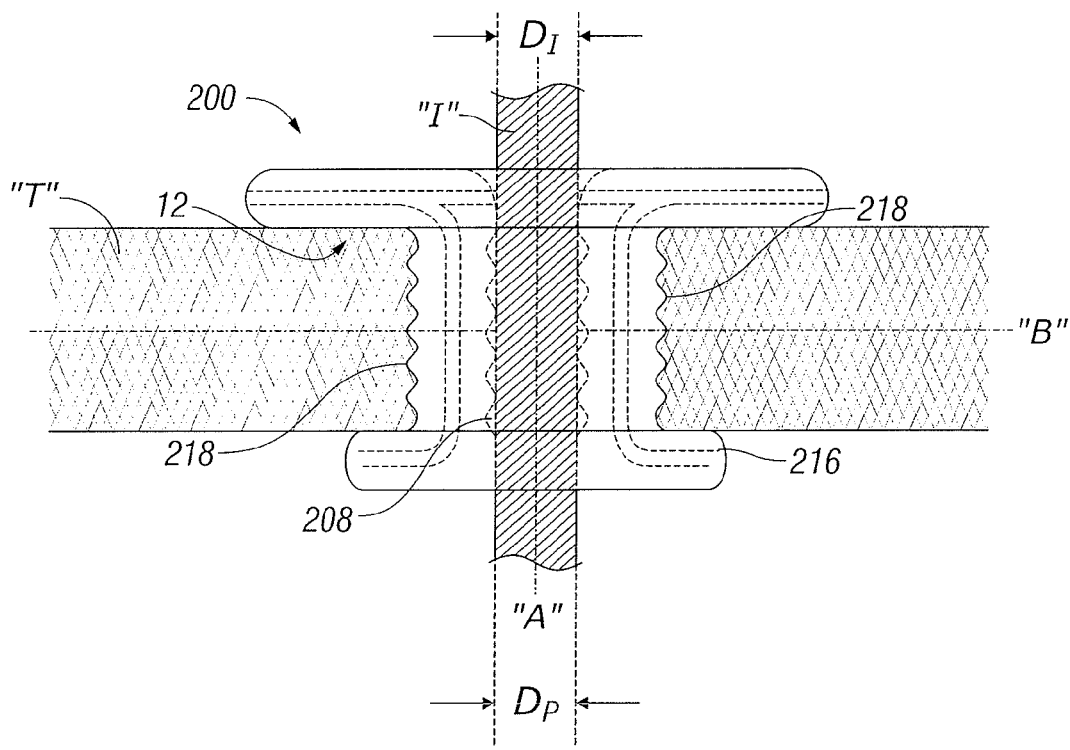
FIG. 3 is a side cross-sectional view of the seal member of FIG. 1 inserted into an incision in tissue and shown in a first condition with a surgical object extending therethrough.

With reference to FIGS. 1A-3, a surgical access apparatus 10 is disclosed that is removably positionable within a percutaneous incision 12 formed in a patient's tissue "T" during the course of a surgical procedure, e.g., a minimally invasive procedure, to facilitate access to a patient's underlying cavities, tissues, organs, and the like with one or more surgical objects "I" (FIG. 3). In one aspect of the present disclosure, surgical access apparatus 10 includes a deployment member 100 that is releasably secured to an elongated seal member 200.

Deployment member 100 is secured to an internal surface 210 of elongated seal member 200 such that at least a portion of deployment member 100 extends proximally of elongated seal member 200. Deployment member 100 may be secured to internal surface 210 through any means suitable for the intended purpose of allowing deployment member 100 to be detached from elongated seal member 200 at the election of the user, including but not being limited to the use of a biocompatible adhesive. In one embodiment, as seen in FIGS. 1A-3, deployment member 100 is configured as a sleeve defining an opening 102 that extends at least partially therethrough. Opening 102 is configured to facilitate grasping of deployment member 100 by a user, e.g., by placing one or more digits therein.

Elongated seal member 200 includes a proximal portion 202, an intermediate portion 204, a distal portion 206, and a passageway 208 defined by internal surface 210 and extending longitudinally through elongated seal member 200 along a longitudinal axis "A".

Proximal portion 202 includes a proximal surface 212 extending outwardly with respect to the longitudinal axis "A" along a transverse axis "B", and defines a first dimension $D_1$. In one embodiment, as seen in FIGS. 1-3, proximal surface 212 may include at least one stiffening member 214. Stiffening member 214 may extend distally from proximal portion 202 and at least partially into intermediate portion 204, as depicted. Alternatively, stiffening member 214 may be substantially annular in configuration and disposed solely within proximal portion 202. Stiffening member 214 may be formed of any biocompatible material suitable for the intended purpose of rigidifying elongated seal member 200 to facilitate the anchoring thereof within tissue, as discussed below.

Intermediate portion 204 extends distally from proximal portion 202. Intermediate portion 204 and defines a second dimension $D_2$ along transverse axis "B" and a length "L". The second dimension $D_2$ of intermediate portion 204 may be either substantially constant along its length "L", or variable.

Distal portion 206 includes a lip 216 extending in transverse relation to the longitudinal axis "A", along axis "B", and defines a third dimension $D_3$. Lip 216 is configured to engage tissue "T" (FIG. 3) when elongated seal member 200 is disposed within percutaneous incision 12, and thereby resist the removal of elongated seal member 200.

The respective first and third dimensions $D_1$, $D_3$ of proximal and distal portions 202, 206 are each greater than the second dimension $D_2$ of intermediate portion 204 such that elongated seal member 200 defines an "hour-glass" shape or configuration to assist in anchoring elongated seal member 200 within tissue "T" (FIG. 3). However, an embodiment in which the second dimension $D_2$ of intermediate portion 204 is substantially equivalent to the respective dimensions $D_1$, $D_3$ of proximal and distal portions 202, 206 is also within the scope of the present disclosure. Additionally, the third dimension $D_3$ of distal portion 206 may be appreciably smaller than the first dimension $D_1$ of proximal portion 202, as shown in FIGS. 1-3, or alternatively, the respective first and third dimensions $D_1$, $D_3$ of proximal and distal portions 202, 206 may be substantially equal.

The outermost surfaces of proximal and distal portions 202, 206 are substantially planar in configuration. However, an embodiment is also contemplated herein in which either or both of proximal and distal surfaces 202, 206, respectively, define surfaces that are substantially arcuate to facilitate the insertion of elongated seal member 200 within incision 12.

Passageway 208 is configured to removably receive surgical object "I" (FIG. 3), as discussed in further detail below. Passageway 208 defines an inner dimension "$D_P$" that is smaller than the outer dimension "$D_I$" of surgical object "I" such that the introduction of surgical object "I" to elongated seal member 200 causes passageway 208 to expand or enlarge outwardly with respect to the longitudinal axis "A" along transverse axis "B". Although the outer dimension "$D_I$" of surgical object "I" will generally lay within the range of about 3 mm to about 15 mm, the employ of surgical objects have substantially larger or smaller outer dimensions is also within the scope of the present disclosure.

Figure 4:
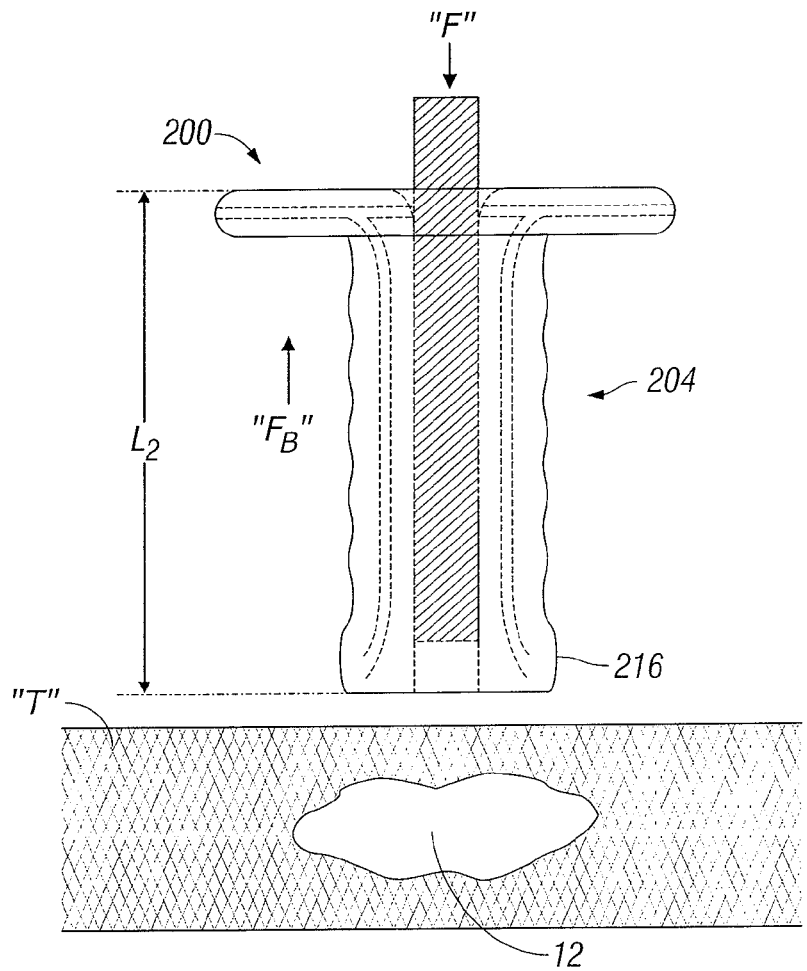
FIG. 4 is a side cross-sectional view of the seal member of FIG. 1 shown in a second condition with the sleeve member inserted therein and secured thereto.

Referring now to FIG. 4 as well, elongated seal member 200 is adapted to transition from a first (or normal) condition (FIGS. 1-3) to a second (or extended) condition (FIG. 4). In the first condition, seal member 200 defines an overall length "$L_1$", and the dimension $D_2$ of intermediate portion 204 is greater than that of the incision 12 to thereby facilitate the anchoring of elongated seal member 200, as discussed in further detail below. To further assist in the anchoring of elongated seal member 200, intermediate portion 204 exhibits a substantially irregular profile in the first condition in which a plurality of tissue engaging surfaces 218 are defined. The contact between tissue engaging surfaces 218 and tissue "T" may also form a substantially fluid-tight seal therebetween. When in the first condition, lip 216 extends outwardly along transverse axis "B" to further facilitate the anchoring of elongated seal member 200 within tissue "T" and resist the removal of seal member 200 therefrom. In the second condition, elongated seal member 200 defines an overall length "$L_2$" that is greater than the length "$L_1$" of the elongated seal member 200 when in the first condition, and intermediate portion 204 exhibits a profile that is substantially more uniform, in that tissue engaging surfaces 218 are substantially less prominent. Additionally, when in the second condition, lip 216 extends generally in the distal direction so as not to inhibit the insertion of elongated seal member 200 within incision 12.

To facilitate the transition of elongated seal member 200 from the first condition to the second condition, the user grasps deployment member 100 and applies a force "F" thereto that is directed distally, thereby advancing deployment member 100 in that direction. As deployment member 100 is advanced, the engagement between deployment member 100 and internal surface 210 causes intermediate portion 204 to elongate, and lip 216 to deflect, in the distal direction. It should be noted that the elongation of elongated seal member 200 during the transition thereof from the first condition to the second condition may cause portions of elongated seal member 200, e.g., intermediate and distal portions 202, 206, respectively, to deform inwardly along transverse axis "B", thereby reducing the dimensions of elongated seal member 200, e.g., the respective dimensions $D_2$, $D_3$ of intermediate and distal portions 202, 206, and further facilitating the insertion of elongated seal member 200 within incision 12.

Elongated seal member 200 may be formed of any suitable biocompatible material that is at least semi-elastic and deformable in nature, e.g., silicon or memory foam. Forming elongated seal member 200 of an elastic material allows elongated seal member 200 to resiliently transition between the first and second conditions thereof, and acts to return elongated seal member 200 to its first condition upon the removal of force "F" from deployment member 100. Forming elongated seal member 200 of a material that is also deformable in nature allows intermediate portion 204 to conform to both the smaller dimensions of incision 12 upon the insertion of elongated seal member 200 therein, and permits passageway 208 to accommodate the larger dimensions of surgical object "I".

Figure 5:
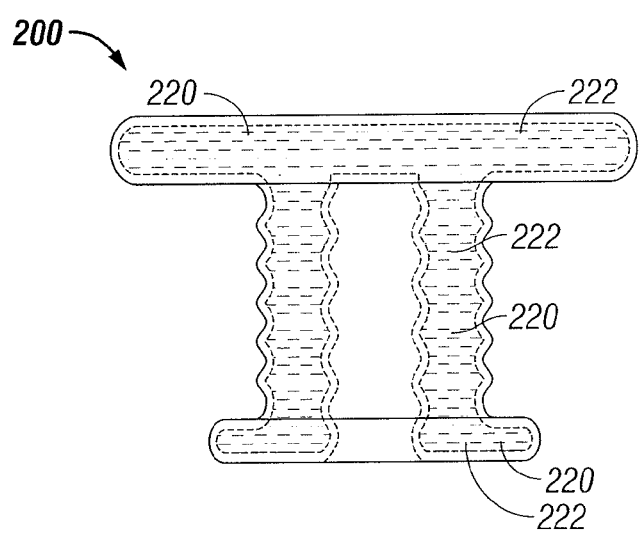
FIG. 5 is a side cross-sectional view of one embodiment of the seal member of FIG. 1 incorporating a fluid disposed within an internal cavity.

Referring to FIG. 5, in one embodiment, the resiliency and deformability of elongated seal member 200 is achieved through the incorporation of one or more fluids 220. Fluid 220 is retained within an internally defined cavity 222. In this embodiment, fluid 220 may be any suitable biocompatible fluid, including but not being limited to air, water, or saline.

With respect now to FIGS. 1-4, the use and function of elongated seal member 200 during the course of a typical minimally invasive procedure will be discussed. Initially, the peritoneal cavity (not shown) may be insufflated with a suitable biocompatible gas such as, e.g., $CO_2$ gas, such that the cavity wall is raised and lifted away from the internal organs and tissue housed therein, providing greater access thereto. The insufflation may be performed with an insufflation needle or similar device, as is conventional in the art. It should be noted that the present disclosure also contemplates the employ of surgical access apparatus 10 during the course of a procedure in which insufflation is not required or utilized.

Either prior or subsequent to insufflation, incision 12 is created in the patient's tissue "T". The dimensions of incision 12 may be varied dependent upon the nature of the procedure. However, when surgical apparatus 10 is employed during the course of procedure performed in an insufflated workspace, for reasons explained just below, it is particularly desirable to incise the tissue "T" so as to create an incision 12 defining dimensions smaller than those defined by intermediate portion 204 when elongated seal member 200 is in its first condition.

Prior to its insertion, elongated seal member 200 is in its first condition. In the first condition, the dimensions of elongated seal member 200, e.g., the respective dimensions $D_2$, $D_3$ of the intermediate and distal portions 202, 206, may prohibit the insertion of elongated seal member 200 into incision 12. To allow for the insertion of elongated seal member 200, the user applies a force "F" to deployment member 100, advancing deployment member 100 distally and transitioning elongated seal member 200 into its second condition. In the second condition, elongated seal member 200 is subject to a proximally directed biasing force "$F_B$" that is created by virtue of the resilient nature of the material comprising elongated seal member 200. Biasing force "$F_B$" resists the influence of force "F" and is exerted upon deployment member 100 through the association between deployment member 100 and elongated seal member 200. Upon transitioning into the second condition, elongated seal member 200 is inserted into incision 12 and force "F" is removed from deployment member 100. Upon the removal of force "F", biasing force "$F_B$" returns elongated seal member 200 to its first condition, thereby urging deployment member 100 proximally. After being restored to its first condition, tissue engaging surfaces 218 engage tissue "T" to thereby assist in securing elongated seal member 200 within the patient's tissue "T". The user may then disengage deployment member 100 from internal surface 210 of passageway 208 by applying a predetermined force thereto, e.g., by pulling or drawing deployment member 100 proximally. Subsequently, the user may introduce one or more surgical objects "I" into passageway 208 such that the minimally invasive procedure may be carried out through apparatus 10.

As indicated above, the deformable nature of the material comprising elongated seal member 200 allows intermediate portion 204 to conform to the smaller dimensions of incision 12 in addition to allowing passageway 208 to expand and accommodate the larger dimensions of surgical object "I". Accordingly, elongated seal member 200 may create substantially fluid-tight seals with both tissue "T" and surgical object "I", thereby substantially preventing the escape of insufflation gas, if any, and facilitating the secure anchoring of elongated seal member 200 within tissue "T" throughout the course of the procedure.

After completing the procedure and withdrawing surgical object "I", elongated seal member 200 may be removed from incision 12. It should be noted that the material comprising elongated seal member 200 allows for the deformation thereof during its withdrawal from incision 12 to thereby avoid any unnecessary trauma to the patient's tissue "T". Thereafter, incision 12 may be closed.

Figure 6:
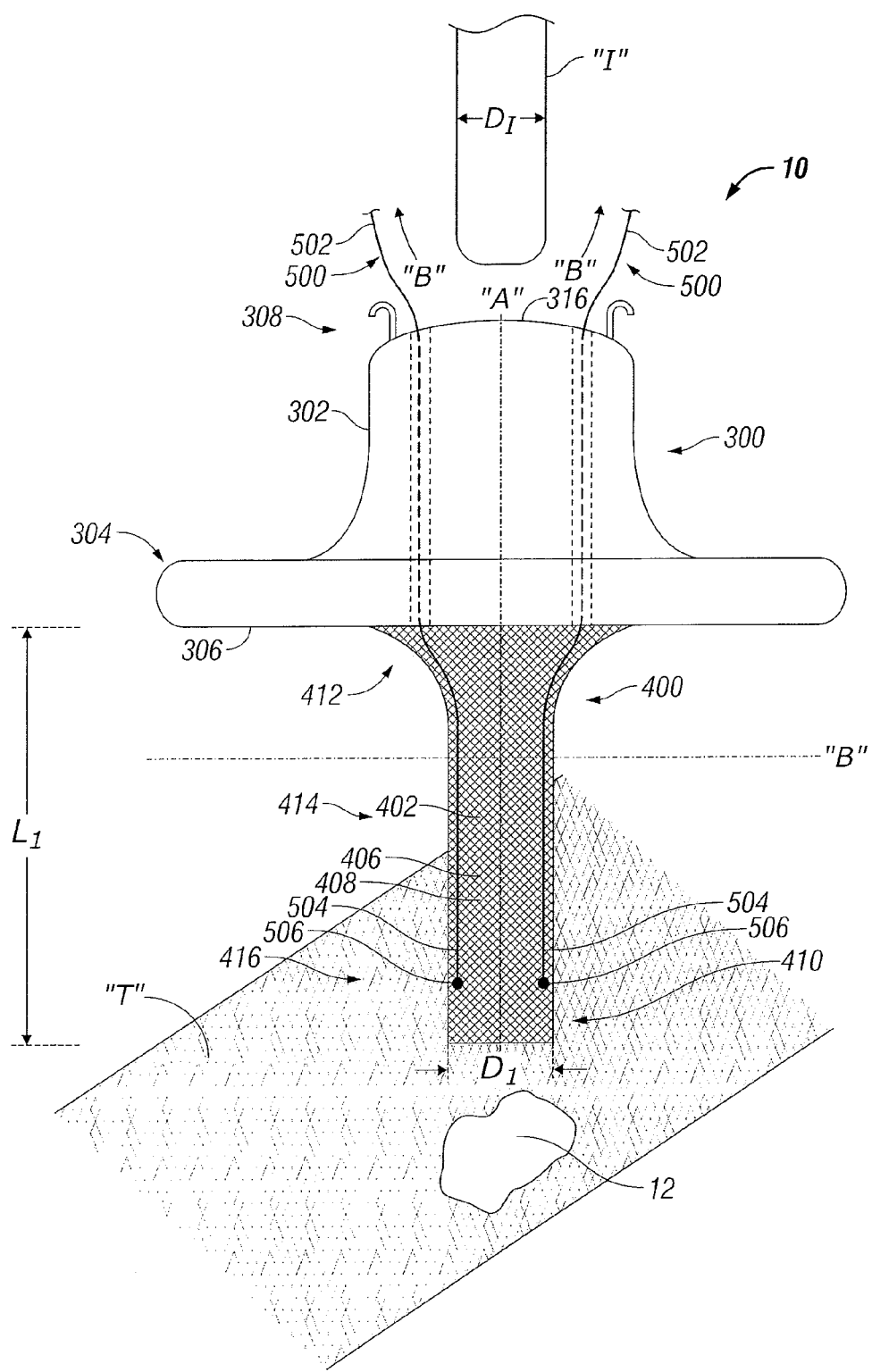
FIG. 6 is a side cross-sectional view of a surgical access apparatus including a housing, an elongate member, shown in a first condition, and filaments in accordance with another aspect of the present disclosure.
Figure 7:
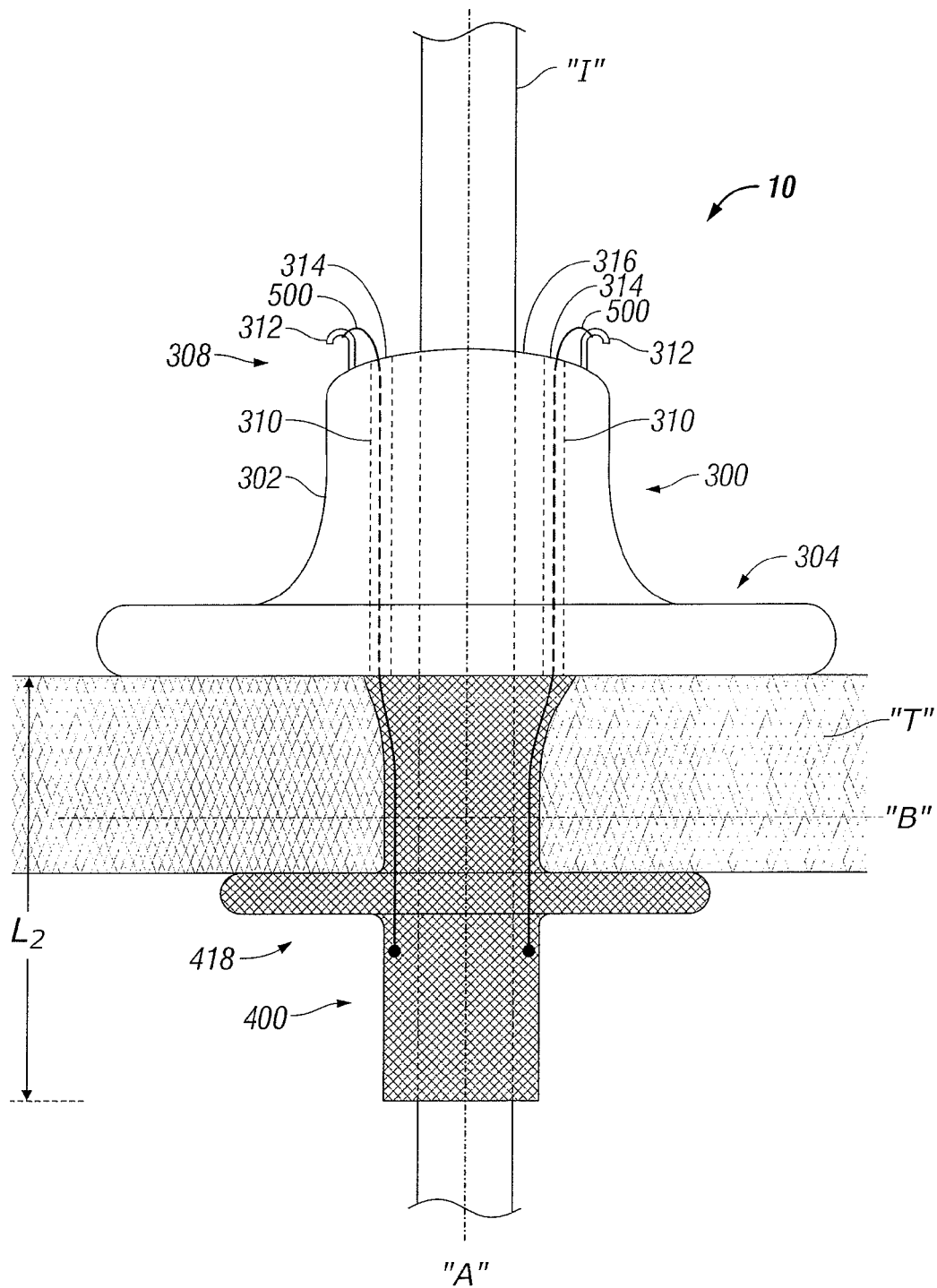
FIG. 7 is a side cross-sectional view of the surgical access apparatus of FIG. 6 with the elongate member shown in a second condition and inserted into an incision in a patient's tissue.

Referring now to FIGS. 6-7, in an alternate aspect of the present disclosure, surgical access apparatus 10 includes a housing 300, an elongated member 400 extending distally from housing 300, and one or more filaments 500 that are secured to the elongated member 400.

Housing 300 defines a longitudinal axis "A" and may be fabricated from any suitable biocompatible material including moldable polymeric materials, stainless steel, titanium or the like. Housing 300 is configured for manual engagement by a user and includes an opening (not shown) extending therethrough that is configured for the reception and passage of a surgical object "I". Housing 300 includes an outer wall 302 which defines a flange 304 having a distal surface 306 and may, optionally, include an internal seal or valve (not shown), such as a duck-bill or zero-closure valve, adapted to close in the absence of surgical object "I". Examples of such an internal seal or valve may be seen in commonly assigned U.S. Pat. No. 5,820,600 to Carlson, et al. and U.S. Pat. No. 6,702,787 to Racenet et al., which issued Oct. 13, 1998 and Mar. 9, 2004, respectively, the entire contents of which are incorporated by reference herein. Housing 300 further includes locking structure 308, which is discussed in further detail below.

Elongated member 400 defines an axial lumen 402 that extends therethrough, along longitudinal axis "A". Lumen 402 is configured for the reception and passage of a surgical object "I". Elongated member 400 is configured as a braid 404 formed of a mesh of biocompatible fibers 406. In one embodiment of elongated member 400, fibers 406 may be formed of a substantially elastic material such that elongated member 400 may expand along an axis "B" that is transverse, e.g., orthogonal, in relation to longitudinal axis "A". However, in an alternate embodiment, fibers 406 may be formed of a substantially inelastic material, e.g., polyamide fiber, stainless steel, or the like, such that elongated member 400 experiences a measure of shortening along longitudinal axis "A" upon the introduction of surgical object "I", further details of which may be obtained through reference to U.S. Pat. No. 5,431,676 to Dubrul et al., the entire contents of which are incorporated by reference herein. The braid 404 may be comprised of fibers 406 having any suitable configuration, including but not being limited to round, flat, ribbon-like, or square.

Figure 8:
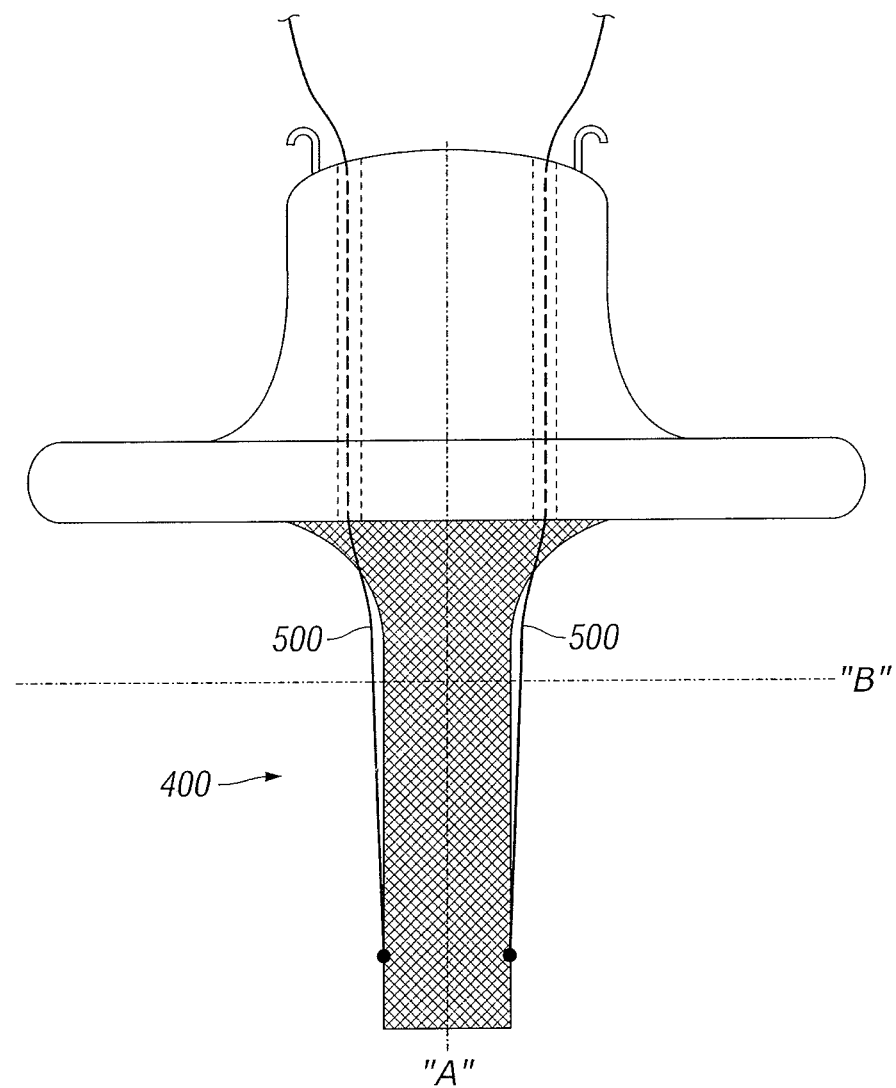
FIG. 8 is a side cross-sectional view of one embodiment of the surgical access apparatus of FIG. 6 with the filaments disposed externally of the elongate member.

Filaments 500 have proximal ends 502 that extend proximally beyond housing 300 and distal ends 504 that are secured to elongated member 400 at attachment points 506. Attachment points 506 may be located at any suitable position along elongated member 400 proximal of a distal-most end 408 thereof, e.g., at a proximal section 410, an intermediate section 412, or a distal section 414. As seen in FIGS. 6-7, in one embodiment, filaments 500 are disposed within lumen 402 of elongated member 400, whereas in an alternate embodiment, filaments 500 are disposed externally of elongated member 400, as seen in FIG. 8. In yet another embodiment, filaments 500 may be interlaced within the mesh comprising the elongated member 400. Filaments 500 may be secured to elongated member 400 at attachment points 506 through any suitable means, such as adhesives. Alternatively, filaments 500 may be integrally formed with elongated member 400 such that filaments 500 constitute proximal extensions of fibers 406. Filaments 500 are used to facilitate the transition of elongated member 400 from a first (or initial) condition (FIG. 6) to a second (or activated) condition (FIG. 7).

In the first condition, elongated member 400 defines an initial length "$L_1$" and an initial outer dimension "$D_1$". Length "L1" may vary depending on the intended usage for apparatus 10, but in general, "$L_1$" will lie substantially within the range of about 10 cm to about 25 cm, although elongate members 400 that are substantially longer or shorter are also contemplated herein. The initial outer dimension "$D_1$" of elongate member is smaller than the dimensions of incision 12 such that elongated member 400 may be inserted and advanced distally through incision 12 will little or no resistance.

Upon the application of a force "F" to filaments 500 in the direction of arrow "B", e.g., by pulling or drawing filaments 500 proximally, elongated member 400 is shortened along the longitudinal axis "A", thereby transitioning into the second condition. In the second condition, elongated member 400 defines a length "$L_2$" that is appreciably less than its initial length "$L_1$". Additionally, in the second condition, elongated member 400 defines a tissue engaging portion 416 having an outer dimension "$D_2$" that is appreciably greater than the outer dimension "$D_1$" of the elongated member 400 in the first condition. Tissue engaging portion 416 contacts the patient's tissue "T" about incision 12 and, in conjunction with flange 304 of housing 300, facilitates the anchoring of apparatus 10. Additionally, tissue engaging portion 416 acts to at least partially form a seal with tissue "T".

As previously indicated, housing 300 of apparatus 10 includes locking structure 308. Locking structure 308 acts to maintain elongated member 400 in the second condition thereof. As seen in FIGS. 5-6, in one embodiment, locking structure 308 includes one or more channels 310 formed in housing 300 and one or more engagement members 312. Channels 310 extend at least partially through housing 300 and have an egress 314 formed either in a proximal-most surface 316 or outer wall 302 of housing 300. In this embodiment, filaments 500 extend through channels 310 such that the proximal ends 502 thereof may be grasped by the user to thereby transition elongated member 400 into the shortened condition thereof. To maintain elongated member 400 in the second condition, the proximal ends 502 of filaments 500 are secured about engagement members 312, e.g., by tying. Engagement members 312 may be any structure suitable for the intended purpose of releasably receiving filaments 500, such as a hook.

Figure 9A:
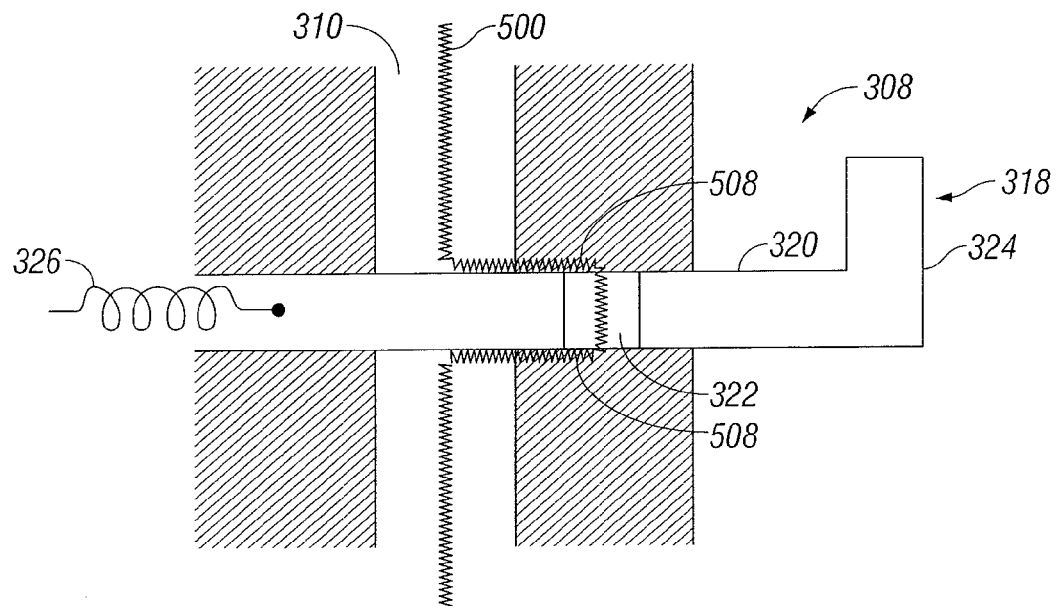
FIG. 9A is a side cross-sectional view of one embodiment of locking structure for use with the surgical access apparatus of FIG. 6 shown in a locked condition.
Figure 9B:
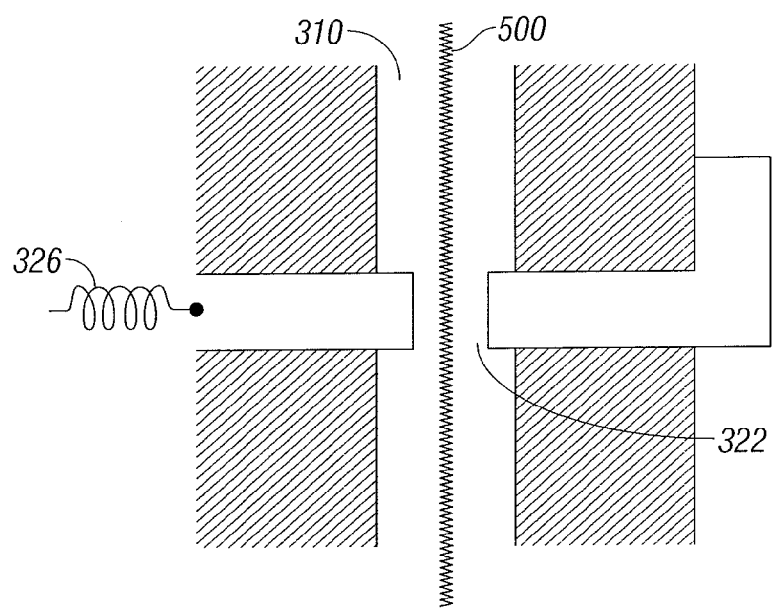
FIG. 9B is a side cross-sectional view of the locking structure of FIG. 9A shown in an open condition.

As seen in FIGS. 9A-9B, in an alternate embodiment, locking structure 308 includes channels 310 and a locking mechanism 318. Locking mechanism 318 includes a locking member 320 having an aperture 322 formed therein, a handle portion 324, and a biasing member 326. Aperture 322 is configured to receive filaments 500 and handle portion 324 is configured for manual engagement by the user to facilitate the transition of locking mechanism 318 between a locked condition (FIG. 9A) and an open condition (FIG. 9B). In the locked condition, aperture 322 is in misalignment with channel 310 such that a portion 508 of filament 500 is disposed between the housing 300 and the locking member 320, effectively prohibiting any movement of filaments 500 and thereby maintaining the second condition of elongated member 400. When locking mechanism 318 is in the open condition, however, at least a portion of aperture 322 is aligned with channel 310 such that filament 500 may freely extend therethrough. Biasing member 326 urges locking mechanism 318 towards the locked condition and may be comprised of any structure or mechanism suitable for this intended purpose, e.g., a spring.

In alternative embodiments, locking mechanism 318 may comprise a single locking member 320 and a single biasing member, or a plurality of locking members engagable with one or more biasing members 326.

Referring again to FIGS. 6-7, the use and function of seal member apparatus 10 will be discussed during the course of a typical minimally invasive procedure subsequent to the formation of incision 12 in the patient's tissue "T".

Prior to the insertion of apparatus 10, elongated member 400 is in its first condition such that distal-most end 408 of elongated member 400 may be inserted into incision 12. The user then advances apparatus 10 distally until flange 304 abuts tissue "T". Thereafter, the user draws filaments 500 proximally, thereby transitioning elongated member 400 into its second condition and forming tissue engaging portion 416. The user may then secure filaments 500 to locking structure 308 to thereby maintain the second condition of elongated member 400 and anchor apparatus 10 within incision 12. Surgical object "I" may then be inserted into and advanced distally through lumen 402 of elongated member 400 to carry out the surgical procedure through apparatus 10. It should be noted that the insertion of surgical object "I" may dilate elongated member 400 outwardly, thereby forcing tubular braid 404 outwardly along transverse axis "B" and into tighter engagement with tissue "T", thereby further securing apparatus 10 and enhancing the quality of the seal formed by the engagement of tissue "T" with flange 304 and tissue engaging portion 416.

After completing the procedure and withdrawing surgical object "I", filaments 500 may be disengaged from locking structure 308, e.g., untied, such that elongate member may return to its initial condition. Apparatus 10 may then be withdrawn from incision 12 and incision 12 may be closed.

Figure 10A:
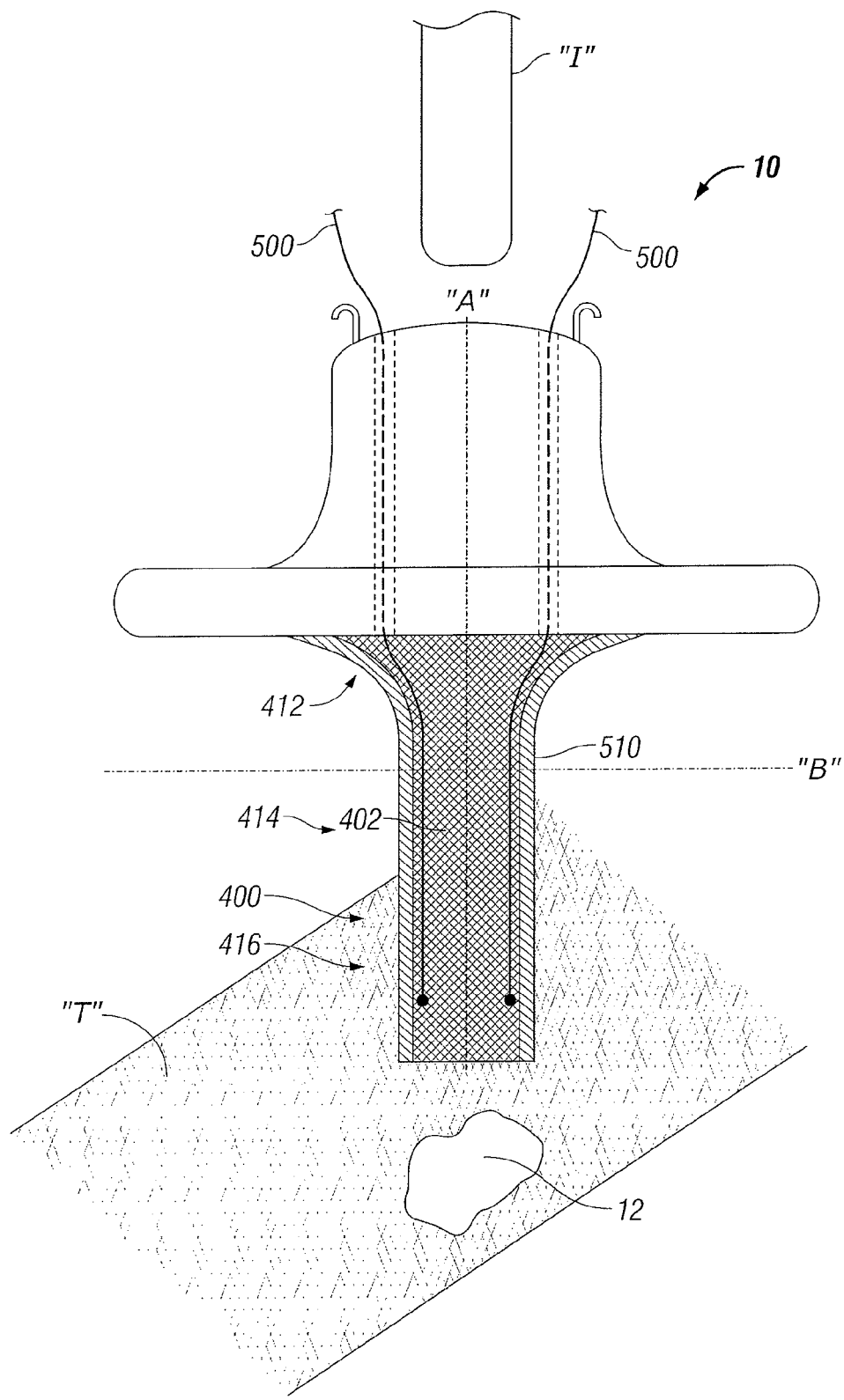
FIGS. 10A-10B are side cross-sectional views of another embodiment of the surgical access apparatus of FIG. 6 including a membrane disposed about the elongate member, the elongate member being respectively shown in its first and second conditions.
Figure 10B:
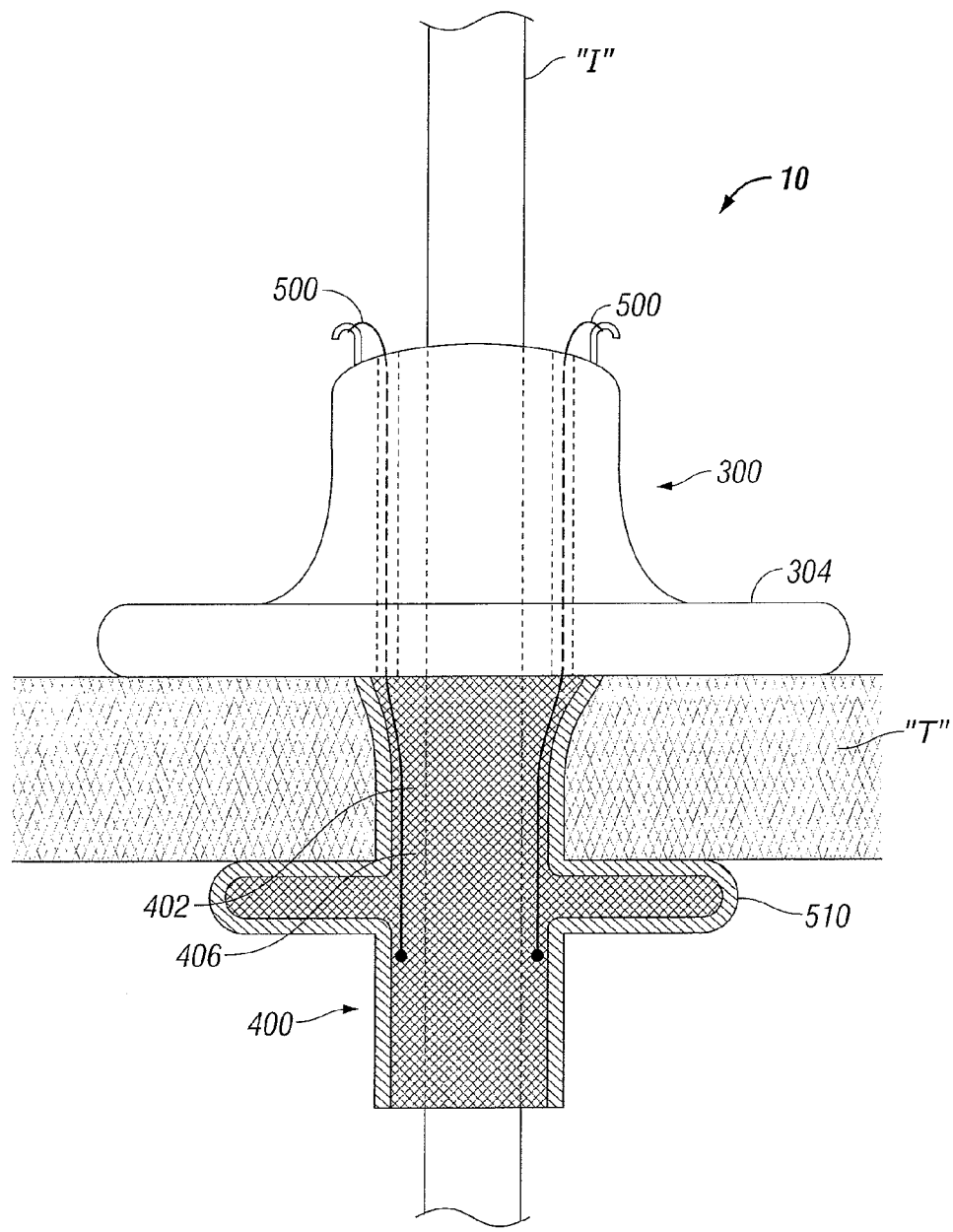

Referring now to FIGS. 10A-10B, in another embodiment, apparatus 10 further includes a membrane 510 that is disposed about elongated member 400. Membrane 510 may be composed of any suitable biocompatible material that is at least semi-resilient in nature and substantially impervious to fluids, e.g., blood or insufflation gas. The incorporation of membrane 510 may facilitate the insertion and passage of one or more surgical objects "I" into and through lumen 402 of elongated member 400, and may constitute the means by which filaments 500 are secured to elongated member 400. Membrane 510 may be disposed about elongated member 400 along its entire length, or in the alternative, membrane 510 may be selectively disposed about individual sections of elongated member 400, e.g. proximal section 410, intermediate section 412, and/or distal section 414.

When disposed about proximal section 410 of elongated member 400, membrane 510 engages the patient's tissue "T" upon the transition of elongated member 400 from the first condition (FIG. 10A) into the second condition (FIG. 10B) thereof. The engagement of membrane 510 with tissue "T", in conjunction with flange 304 of housing 300, creates a substantially fluid-tight seal about incision 12, thereby substantially preventing the escape of any fluids, e.g. blood or insufflation gas, if any, about apparatus 10.

As previously discussed with respect to the embodiment of FIGS. 6-7, the introduction of surgical object "I" to elongated member 400 forces tubular braid 404 outwardly along transverse axis "B". In the embodiment of FIGS. 10A-10B, membrane 510 would also be forced outwardly and into tighter engagement with tissue "T". Accordingly, membrane 510 may act to further anchor apparatus 10 within tissue "T" and tighten the seal created therewith by tissue engaging portion 416 and flange 304.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical access apparatus for positioning within an incision in tissue to facilitate access to an underlying surgical site, the surgical access apparatus comprising:
    a housing configured to removably receive at least one surgical object;
    an elongated member including a tubular braid formed of a mesh of fibers, the elongated member having proximal and distal ends and defining a longitudinal axis, the elongated member extending distally from the housing and defining an axial lumen configured to allow the at least one surgical object to pass therethrough, the elongated member being adapted to transition from a first extended condition, in which the elongated member is configured for at least partial insertion within the incision, and a second compressed condition, in which the elongated member defines a tissue engaging portion configured to facilitate anchoring of the elongated member relative to the incision, wherein, when in the second compressed condition, the tissue engaging portion is expanded to define a transverse dimension orthogonal to the longitudinal axis greater than a corresponding transverse dimension of the entire remaining portion of the elongated member, the tissue engaging portion being spaced along the longitudinal axis relative to the distal end of the elongated member; and
    at least one flexible filament secured to the elongated member and extending proximally relative thereto, the at least one filament being dimensioned such that drawing the at least one filament proximally transitions the elongated member from the first extended condition to the second compressed condition.

2. The surgical access apparatus of claim 1, wherein the at least one filament is disposed within the lumen of the elongated member.

3. The surgical access apparatus of claim 1, wherein the at least one filament is secured to an external surface of the elongated member.

4. The surgical access apparatus of claim 1, further including a membrane disposed about at least a proximal portion of the elongated member to facilitate anchoring of the elongated member within the tissue.

5. The surgical access apparatus of claim 1, wherein the housing includes locking structure configured to engage the at least one filament and thereby maintain the second compressed condition of the elongated member.

6. The surgical access apparatus of claim 5, wherein the locking structure includes at least one channel formed in the housing, the at least one channel being configured to at least partially receive the at least one filament.

7. The surgical access apparatus of claim 1, wherein the fibers are substantially elastic.

8. The surgical access apparatus of claim 1, wherein the at least one filament is configured to extend proximally from the housing and positioned to be accessed by a user.

9. The surgical access apparatus of claim 1, wherein the tissue engaging portion is spaced relative to both the proximal end and the distal end of the elongated member.

10. The surgical access apparatus of claim 1, wherein the at least one filament is interlaced with the tubular braid of the elongated member to connect the filament to the elongated member.

11. A surgical access apparatus for positioning within an incision in tissue to facilitate access to an underlying surgical site, the surgical access apparatus comprising:
    a housing configured to removably receive at least one surgical object, the housing having at least one channel;
    an elongated member including a tubular braid formed of a mesh of fibers, the elongated member having proximal and distal ends and defining a longitudinal axis, the elongated member extending distally from the housing and defining an axial lumen configured to allow the at least one surgical object to pass therethrough, the elongated member being adapted to transition from a first extended condition, in which the elongated member is configured for at least partial insertion within the incision, and a second compressed condition, in which the elongated member defines a tissue engaging portion configured to facilitate anchoring of the elongated member relative to the incision, wherein, when in the second compressed condition, the tissue engaging portion is expanded to define a transverse dimension orthogonal to the longitudinal axis greater than a corresponding transverse dimension of the entire remaining portion of the elongated member, the tissue engaging portion being spaced along the longitudinal axis relative to the distal end of the elongated member;
    at least one filament secured to the elongated member and extending proximally relative thereto, the at least one filament being at least partially received within the at least one channel of the housing, the at least one filament being dimensioned such that drawing the at least one filament proximally transitions the elongated member from the first extended condition to the second compressed condition; and
    a locking member repositionable between unlocked and locked positions, the locking member defining a channel therethrough configured to at least partially receive the at least one filament, the channel of the locking member and the channel of the housing being substantially aligned when the locking member is in the unlocked position, the locking member configured to engage the at least one filament and thereby maintain the second compressed condition of the elongated member when in the locked position.

12. The surgical access apparatus of claim 11, wherein the channel of the locking member and the channel of the housing are substantially misaligned when the locking member is in the locked position.

13. The surgical access apparatus of claim 12, wherein the locking member is biased towards the locked position by a biasing member.

14. A surgical access apparatus, which comprises:
    a housing;
    an elongated member extending from the housing and having proximal and distal ends, the elongated member defining a longitudinal axis and an axial lumen for passage of a surgical object, the elongated member having a tissue engaging segment dimensioned and configured to transition between a first condition where the tissue engaging segment defines a first transverse dimension to permit insertion through tissue, and a second condition where the tissue engaging segment is caused to expand to define a second transverse dimension greater than the first transverse dimension and greater than corresponding transverse dimensions of portions of the elongated member proximal and distal of the tissue engaging segment when the tissue engaging segment is in the second condition, to thereby facilitate anchoring of the elongated member within the tissue, the tissue engaging segment being spaced along the longitudinal axis at a position intermediate the proximal and distal ends of the elongated member;

a flexible filament secured to the elongated member, the filament being dimensioned for manipulation such that movement of the filament along the longitudinal axis causes the tissue engaging segment to transition between the first condition and the second condition, the filament configured to extend proximally from the housing and positioned to be accessed by a user; and a resilient membrane mounted over at least the tissue engaging segment of the elongated member, the resilient membrane being radially outward of the tissue engaging segment.

15. The surgical access apparatus according to claim 14 wherein the tissue engaging segment of the elongated member is dimensioned to transition from the first condition to the second condition upon proximal longitudinal movement of the filament.

16. The surgical access apparatus according to claim 15 wherein the housing includes a lock, the lock dimensioned to selectively engage the filament to maintain the tissue engaging segment in the second condition.

17. The surgical access apparatus according to claim 16 wherein the lock is movable between a locked condition securing the filament and a release condition releasing the filament.

18. The surgical access apparatus according to claim 17 wherein the lock is normally biased toward the locked condition.

19. A surgical access apparatus, which comprises:
a housing;
an elongated member extending from the housing and having proximal and distal ends, the elongated member defining a longitudinal axis and an axial lumen for passage of a surgical object, the elongated member having a tissue engaging segment dimensioned and configured to transition between a first condition where the tissue engaging segment defines a first transverse dimension to permit insertion through tissue, and a second condition where the tissue engaging segment is caused to expand to define a second transverse dimension greater than the first transverse dimension and greater than corresponding transverse dimensions of portions of the elongated member proximal and distal of the tissue engaging segment when the tissue engaging segment is in the second condition, to thereby facilitate anchoring of the elongated member within the tissue, the tissue engaging segment being spaced along the longitudinal axis at a position intermediate the proximal and distal ends of the elongated member, at least the tissue engaging segment of the elongated member including a braid;

a flexible filament secured to the elongated member, the filament being dimensioned for manipulation such that proximal longitudinal movement of the filament along the longitudinal axis causes the tissue engaging segment to transition between the first condition and the second condition;

a resilient membrane mounted over at least the tissue engaging segment of the elongated member, the resilient membrane being radially outward of the tissue engaging segment; and wherein the housing includes a lock dimensioned to selectively engage the filament to maintain the tissue engaging segment in the second condition, the lock being movable between a locked condition securing the filament and a release condition releasing the filament, the lock being normally biased to the locked position.

20. The surgical access apparatus according to claim 19 wherein the filament is secured to the tissue engaging segment.

* * * * *